(12) United States Patent
Vanderhorst et al.

(10) Patent No.: US 11,207,262 B2
(45) Date of Patent: Dec. 28, 2021

(54) STYLING COMPOSITION FOR CURLY HAIR

(71) Applicant: Kao USA Inc., Cincinnati, OH (US)

(72) Inventors: Heather Vanderhorst, Cincinnati, OH (US); Christine Sarosy, Cincinnati, OH (US)

(73) Assignee: KAO USA INC., Cincinnati, OH (US)

( * ) Notice: Subject to any disclaimer, the term of this patent is extended or adjusted under 35 U.S.C. 154(b) by 607 days.

(21) Appl. No.: 15/479,554

(22) Filed: Apr. 5, 2017

(65) Prior Publication Data
US 2018/0289611 A1   Oct. 11, 2018

(51) Int. Cl.
*A61Q 5/06* (2006.01)
*A61K 8/87* (2006.01)
*A61K 8/81* (2006.01)
*A61K 8/34* (2006.01)

(52) U.S. Cl.
CPC ................ *A61K 8/87* (2013.01); *A61K 8/342* (2013.01); *A61K 8/8117* (2013.01); *A61Q 5/06* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 2003/0206880 A1* | 11/2003 | Khoshdel | A61K 8/738 424/70.13 |
| 2005/0209428 A1 | 9/2005 | Tamareselvy | |
| 2006/0013785 A1 | 1/2006 | Lauscher et al. | |
| 2012/0244083 A1* | 9/2012 | Schmid | A61K 8/046 424/47 |
| 2014/0342968 A1 | 11/2014 | Hourigan | |
| 2015/0004117 A1 | 1/2015 | Tan et al. | |
| 2016/0175236 A1* | 6/2016 | Tan | A61K 8/87 424/43 |

\* cited by examiner

*Primary Examiner* — Jyothsna A Venkat
(74) *Attorney, Agent, or Firm* — Frost Brown Todd LLC

(57) ABSTRACT

The present application discloses a hairstyling composition, particularly for curly hair, which produces tight, long-lasting curls without requiring the use of high heat applied to the hair. The composition comprises a sulfonate-based copolymer (such as sodium polystyrene sulfonate), an aqueous polyurethane dispersion (such as polyurethane-34) and a cosmetically-acceptable carrier (such as water). The method of styling hair using the defined composition, without requiring the application of high heat to the hair, is also disclosed.

7 Claims, 3 Drawing Sheets

STYLING COMPOSITION FOR CURLY HAIR

BACKGROUND

The present invention relates to hairstyling compositions, such as hair styling creams, hair sprays or mousses, especially for curly hair, which produce tight long-lasting curls without requiring the use of high heat on the hair.

Compositions for styling hair are known, such as, for example, hair spray compositions, hair gels and mousses, hair volumizing compositions, hair smoothing creams, lotions, serums, oils and clays. The goal of many hairstyling compositions include holding or fixing the hair in a particular shape, increasing or imparting volume to the hair, and/or to smoothing the hair, for example, to decrease or eliminate the appearance of frizz.

Drawbacks associated with current products for styling hair include that the product is often sticky or tacky and/or often produces a film that imparts a sticky or tacky feel, as well as styled hair appears stiff and the film is hard and brittle. Hair stylists refer to the hair as "untouchable". The hair style will not hold if any mechanical force is applied to the hair since the hard and brittle residual films will fracture. Even a simple action such as hand touching, leaning back against a chair, or putting on a jacket can fracture the film leading to loss of the desired hair style. Consumers then consider that the applied current product has failed since it did not maintain the hair in its original style or shape, and the hair feels unpleasant.

Many conventional curly hairstyling compositions utilize polymers having a high $T_g$ (glass transition temperature). These products are designed for use with a flat styling iron or a hair dryer/blow dryer that produces temperatures above the $T_g$ of the polymer in order to maximize its spreading and deposition on hair. When these styling compositions are applied to hair without the use of high heat (for example, when they are air-dried), a substandard result is usually achieved, including loss of curl throughout the day. Even if a product is able to produce all day lasting curls, they often leave the hair stiff and crunchy. Further, many traditional curl products produce curls that lack bounce and movement. The present invention overcomes these challenges to produce an all day lasting curl without the need for high heat, which is inconvenient and can damage the hair.

Many hairstyling compositions are known in the art. Several examples of such compositions follow.

U.S. Published Patent Application 2015/0004117, Tan et al (L'Oreal), published Jan. 1, 2015, discloses hairstyling compositions (which can be hair sprays) containing at least two latex polymers, at least one of which is a film-forming polymer. Polyurethane materials (such as Baycusan C1001) and polystyrene materials are disclosed. There is no discussion of the use of PSS (sodium polystyrene sulfonate materials) in the disclosed compositions.

U.S. Published Patent Application 2006/0013785, Lauscher et al, published Jan. 19, 2006, describes hair setting gels which are said to provide hair setting capabilities together with UV protection for the skin and hair. The gels comprise a gel former (polyurethane, but not polyurethane-34, is disclosed), a UV filter, and a hair-fixing polymer (which can be PSS). PSS is disclosed in a very long list of hair setting polymers; it is not preferred or exemplified in this application. This application has been abandoned in the USPTO.

U.S. Published Patent Application 2005/0209428, Tamareselvy (Noveon), published Sep. 22, 2005, describes a polyurethane which is said to be useful in a hair fixative product; the disclosed polymer appears to be different from polyurethane-34. The disclosed polymer can optionally be used in combination with known hair fixative polymers. PSS is included in a long list of hair fixative polymers, but is not preferred or exemplified in any way. This application has been abandoned in the USPTO.

It would be desirable to formulate a hairstyling product which provides tight long-lasting curls, but without the stiffness and crunchiness of styling polymers typically used on hair, as well as without requiring the need for application of high heat to the hair, which can damage hair under some circumstances. Curly-haired consumers also desire to have their hair maintain the ability to be touched, such as moving their fingers through their hair or wind blowing through their hair without losing style and shape or creating frizzy hair. These are the benefits provided by the present invention.

SUMMARY

The present invention relates to a hairstyling cosmetic composition which comprises:

(a) a sulfonate-based copolymer (such as a polystyrene sulfonate salt);

(b) an aqueous polyurethane dispersion (such as polyurethane-34); and (c) a cosmetically-acceptable carrier.

In some compositions, the weight ratio of aqueous polyurethane dispersion to sulfonate-based copolymer is from about 2:1 to about 10:1. The composition may additionally contain from about 0.1% to about 7% of at least one fatty alcohol in order to provide conditioning to the hair.

The present invention also encompasses a method of using the hairstyling composition, that composition comprising:

(a) a sulfonate-based copolymer;

(b) an aqueous polyurethane dispersion; and (c) a cosmetically-acceptable carrier, wherein the composition is applied, in a hairstyling effective amount, to the hair and the composition is permitted to air-dry on the hair.

As used herein, all percentages and ratios given are "by weight", unless otherwise specified. Further, all references, articles, patents, and published patent applications referred to in this application are incorporated by reference herein, unless specified otherwise.

DETAILED DESCRIPTION

Figure 1A:
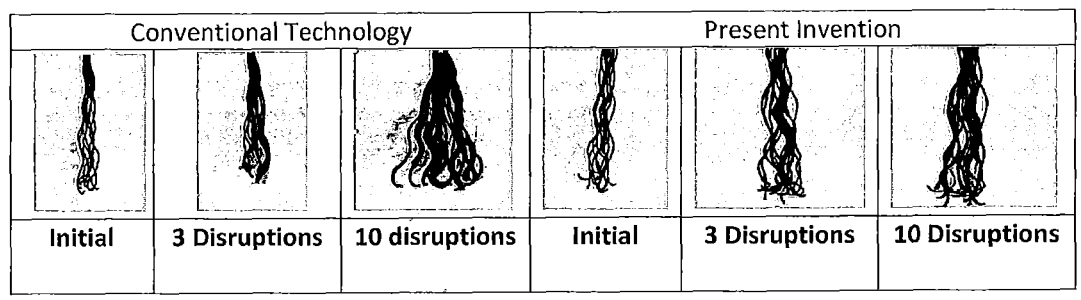
FIGS. 1A-1D show comparisons of the hairstyling properties of a composition of the present invention against commercially-available products.

The present invention is based on the discovery that a specific blend of polymers produces tight, long-lasting curls in hair without the need for application of high heat. Various hairstyling polymers were screened through a variety of test methods, including the 3-point bend testing, curl retention, springiness, curl snap, mannequin and tress evaluation, for properties that would produce this benefit. The unique characteristics of polyurethane-34 and similar materials produced superior results. Importantly, it was discovered that the addition of a sulfonate polymer enhanced the benefits provided by polyurethane-34.

Polyurethane-34's high $T_g$ portion imparts stiffness and hold to the hair while its low $T_g$ portion imparts softness and flexibility. These properties are highlighted through the addition of the anionic film-forming polymer, sodium polystyrene sulfonate (PSS). PSS provides the flexibility and hold required to enhance the consumer benefit provided by the compositions of the present invention.

In one embodiment, polyurethane-34 and sodium polystyrene sulfonate provide a unique combination that produces tight curls after just air drying the hair. In addition, fatty alcohols may be added to the present composition in order to provide additional hair conditioning benefits.

Thus, there are three essential elements of the compositions of the present invention:
(a) one or more sulfonate-based copolymers;
(b) one or more aqueous polyurethane dispersions; and
(c) a hair-compatible cosmetically-acceptable carrier.

Each of these components will be discussed in detail below.

Aqueous Polyurethane Dispersion

The compositions of the present invention include an effective hairstyling amount of an aqueous polyurethane dispersion. Typically, the compositions will include from about 1.5% to about 10%, for example, from about 3% to about 7% of the aqueous polyurethane dispersion.

Examples of such materials include polyurethane-32, polyurethane-34, polyurethane-35, and polyurethane-48. One such material is polyurethane-34 which is the generic INCI name for a polyurethane polymer sold under the Baycusan C1001 tradename from Covestro, formerly Bayer. It is sold as a 32% polymer solution. Polyurethane-34 can be included in hairstyling compositions in any desired amount, with the precise amount based on efficacy and formulation considerations. The material is described in U.S. Published Patent Application 2014/0342968, Hourigan (Colgate-Palmolive Company), published Nov. 20, 2014, incorporated herein by reference.

The material is a colloidal system of a high molecular weight polyurethane polymer dispersed in water. An internal emulsifier is incorporated into the polymer backbone to ensure stability of the dispersion. The polymer was specifically designed as a film-former for hairstyling products. Its unique structure provides a balance of elasticity, hydrophobicity and washability. The material shows good compatibility with a wide range of cosmetic ingredients including common synthetic and natural thickeners, such as Carbopol and xanthan gum, as well polar solvents like ethanol. The material exhibits excellent high humidity curl retention, strong elastic memory, non-tacky feel, excellent sprayability, high gloss, and it is easily removed from the hair by shampooing.

Another related material is Baycusan C1008 which is similar to polyurethane-34 but is specifically designed to enable formulators to manufacture hair sprays with firm and lasting hold. Baycusan C1008 is also known by the INCI name polyurethane-48. This material provides a hold which is flexible, as well as firm and lasting, but without the stiff and sticky feeling one frequently finds with hair styling polymers. This material is an aqueous dispersion based on adipic acid, 1,6-hexanediol, neopentyl glycol, isophorone diisocyanate, isophorone diamine, and N-(2-aminoethyl)-3-aminoethanefulfonic acid, sodium salt.

Polyurethane-34, as well as its related polymers, is comprised of both hard segments and soft segments. The hard segments have a relatively high $T_g$ monomer and they impart stiffness and hold to the hairstyling polymer as a whole. The softer segments are made up of low $T_g$ monomers having a low molecular weight; these segments impart a softness and flexibility to the polymer as a whole. At least a portion of the polyurethane monomer has a low $T_g$. Thus, the entire polymer is a unique combination of high and low $T_g$ monomeric units. The low $T_g$ monomeric units (having a $T_g$ of about −51.5° C.) do not require high heat in order to set them in the hair.

Sulfonate-Based Copolymer,

The present invention also includes an effective hairstyling amount of a sulfonate-based hairstyling copolymer. Typically, the compositions of the present invention will include from about 0.5% to about 7%, such as from about 1% to about 4%, of the sulfonate-based copolymer material. The sulfonate-based copolymer material is an anionic film-forming polymer which includes a sulfonate pendant group and which provides a styling and hold benefit when applied to hair. Examples of such polymers include polyacrylamidomethylpropane sulfonic acid, sodium benzotriazoyl butylphenol sulfonate, and disodium distyrylbiphenyl disulfonate. A preferred material is the polystyrene sulfonate salts (or poly(4-vinyl benzene sulfonic acid)) which has the following general formula:

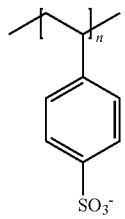

An example of such a material is sodium polystyrene sulfonate (PSS). Sodium polystyrene sulfonate is a unique polymer that provides hair fixative properties, other sulfonic acid-like polymers are mainly used as surfactants or in skin care applications. The sulfonate-based hairstyling copolymers are anionic film-forming polymers which constrict upon drying after application to hair. The polymers prevent fly-a-ways, provide flexibility and hold, and protect the hair from heat damage. When used together with the polyurethane materials, discussed above, these two polymers provide a unique combination of high and low $T_g$ polymers which provide tight curls after just air drying (without requiring the application of high heat to hair).

Exemplary compositions of the present invention have a weight ratio of aqueous polyurethane dispersion:sulfonated-based copolymer of from about 2:1 to about 10:1, such as from about 2:1 to about 5:1.

Cosmetically-Acceptable Carrier

The carriers utilized in the present invention must be both compatible with the other ingredients which are included in the hairstyling compositions, and also be compatible with the hair and scalp (i.e., not cause damage to the hair and/or scalp when applied). The particular carriers utilized will, at least to some extent, depend upon the other components included in the composition, as well as the physical form which the composition may take. Thus, in at least certain exemplary embodiments, the compositions may be in the form of hairstyling compositions in any form, such as, for example, gels, creams, foams, lotions, emulsions, or liquids that may be sprayed onto or otherwise applied to the hair. In various embodiments, the compositions may be provided in the form of a cream, a gel, a liquid, a mousse, or a spray. In at least certain embodiments (e.g., liquids, gels, mousses, creams, foams, lotions), the composition may be applied to the hair by first applying an amount of the composition to the hands, and then working the composition into the hair with the hands. In other embodiments, the composition may be applied directly onto the hair, such as by spraying. The composition generally is applied to the hair as a leave-on treatment. Preferred compositions are a mousse, cream or lotion. The viscosity of the compositions is generally from about 15,000 to about 40,000 cps.

The vehicles (carriers) utilized in the present compositions are well-known in the hair care arts and selection of them will depend, to a large degree, on the physical form the composition is to take, as well as the other components to be included in the composition. Examples of such vehicles include water, lower alcohols, and water/alcohol mixtures. Water is a preferred vehicle for use in the present compositions. Typically, the compositions contain from about 50% to about 95%, such as from about 65% to about 90%, of the vehicle.

Fatty Alcohols

The compositions of the present invention may optionally contain from about 0.1% to about 7% of a fatty alcohol material to provide hair conditioning benefits to the users' hair. The alcohols utilized typically contain from about $C_{10}$ to about $C_{24}$ carbon chain lengths. The alcohols may be straight chain or branched, and may be saturated or unsaturated. Examples of such fatty alcohols include cetearyl alcohol, stearyl alcohol, behenyl alcohol, cetyl alcohol, myristyl alcohol, lauryl alcohol, isostearyl alcohol, oleyl alcohol, and mixtures thereof. Long chain fatty alcohol hair conditioning materials are well-known to those skilled in the arts and those known materials may be included in the compositions of the present invention to provide a desired hair conditioning benefit.

Compositions according to various embodiments of the present invention may further comprise additional components that are typically used in hairstyling compositions. Such components are known to those skilled in the hairstyling art, or are within the ability of those of skill in the art to determine and select depending on the particular application or properties desired, such as, for example, the particular component and/or amount thereof. Such components include, but are not limited to, coalescents; plasticizers; thickeners; quaternary ammonium materials to provide hair conditioning (e.g., cocotrimonium methosulfate); preservatives (such as disodium EDTA), surfactants (such as Trideceth or Ceteareth-25), silicone conditioners (such as silicone quaternium-18), materials which provide benefits to the hair (e.g., jojoba oil or Abyssinian oil), perfumes, colorants or other aesthetic additives.

In various embodiments, the composition described herein may have a pH ranging from about 2 to about 9, such as from about 3 to about 8, or from about 4 to about 7.

Conventional procedures are used for making the compositions of the present invention. An example of such a process includes combining water and the sodium polystyrene sulfonate in the main vessel and mixing the materials together until homogenous. The mixture is then heated to about 80° C. In a separate vessel, add the combined fatty alcohols and heat to about 80° C. Combine the contents of the fatty alcohols with the main vessel once both vessels reach about 80° C. Continue mixing for about 10 to about 20 minutes. Homogenize the combined mixture for about 3 minutes. Begin cooling, and then at about 50° C., add the polyurethane-34 dispersion. Continue cooling to room temperature. Add the preservative once the mixture is cooled.

The way in which the compositions of the present invention are used depends at least to some degree on the particular form which the composition takes. Generally, a hairstyling effective amount of the composition is applied to the hair, which may either be in dry or in damp form. By "hairstyling effective amount" is meant an amount of the composition which is effective to provide the desired degree of hairstyling and conditioning, but not so much as to provide an undesirable look and feel of the composition on the hair. Typically, an effective amount of the hairstyling composition comprises from about 2 to about 8 grams of the composition. If the composition is a hair spray, it may be sprayed directly onto the hair (and the hair is generally dry). If the composition is formulated as a mousse, cream or liquid, the effective amount is generally placed in the hands of the user and the user then uses his/her hands to work the composition into wet hair. The hair is then styled using a comb or brush. High heat does not have to be applied to the hair (and preferably is not applied to the hair) in order to achieve the desired styling benefit.

Example

A cream product of the present invention having the following composition is made as described below:

| INCI Name | w/w % |
|---|---|
| DI Water | To 100 |
| Disodium EDTA | 0.00-0.10 |
| Hydroxypropyl Methylcellulose | 1.00-5.00 |
| Sodium Polystyrene Sulfonate | 1.00-5.00 |
| Ceteareth-25 | 0.10-1.00 |
| Cetearyl Alcohol | 1.00-5.00 |
| Stearyl Alcohol | 0.10-1.00 |
| Behenyl Alcohol | 0.00-0.10 |
| Cetyl Alcohol | 0.10-1.00 |
| Polyurethane-34 | 1.00-5.00 |
| Polyacrylamide (and) C13-14 Isoparaffin (and) Laureth-7 | 1.00-5.00 |
| Cocotrimonium Methosulfate | 0.10-1.00 |
| Laureth-3 | 0.10-1.00 |
| Water (and) Silicone Quaternium-18 (and) Trideceth-6 (and) Trideceth-12 | 0.10-1.00 |
| Preservative | 0.10-1.00 |
| Jojoba Oil | 0.10-1.00 |
| Abysinnian Oil | 0.00-0.10 |
| Fragrance | 0.00-0.10 |

The water and sodium polystyrene sulfonate components are combined in a main vessel and the mixing is continued until the mixture is homogenous. The mixture is heated to about 80° C. In a separate vessel, the fatty alcohols are combined and heated to about 80° C. The contents of the fatty alcohol vessel and the main vessel are combined once both vessels reach about 80° C. Mixing is continued for about 10-20 minutes. The combined mixture is homogenized for about 3 minutes. Begin cooling, and then at about 50° C., add the polyurethane-34 dispersion. Continue cooling to room temperature. The preservative is added once the mixture is cooled. The product formed is a cream (crème) hair styling product.

About 5 grams of the product is placed on the hands of the consumer. The product is then worked through damp hair by the user using her hands until the composition is well dispersed through the damp hair. The hair is then styled with a comb and brush to produce the desired hairstyle.

FIG. 1 (1A-1D) of the present application shows a comparison between commercially-available styling products and a product of the present invention, particularly on curly, wavy hair.

The three products tested were a commercially-available mousse product, commercially-available gel product and the styling crème of the present invention, described above. In each case, hair tresses were wet with water, then dried and the hair-setting material (about 0.50 g) was then distributed through the tresses using fingers. The treated hair was not subject to drying of any kind and particularly was not subjected to high heat. The tresses themselves were evaluated and the curl retention of each of the three compositions was also evaluated. With respect to the commercially-available mousse product, a lower hold was seen and the product didn't control the natural waves and curls of the hair tresses. With respect to the commercially-available gel product, stronger hold than the mousse product was seen but the gel product also didn't control the natural waves and curls of the hair tresses. Finally, the product of the current invention showed smaller, tighter hair bundles, springy and elastic waves and curls, control and enhancement of the curls found in the tresses, and a strong hold but without the stiffness seen with the second commercial product. Thus the product of the present invention exhibited strong hold, without any stiffness in the waves or curls, and without requiring any application of high heat to the hair.

In FIG. 1A, with the conventional technology, the weld points created by these stiff, brittle polymers break once disrupted, leaving the ends misaligned and frizzy, with overall loss of curl definition. With the present invention, the weld points created by the flexible polymers do not break once disrupted leaving the curls aligned and frizz-free.

Figure 1B:
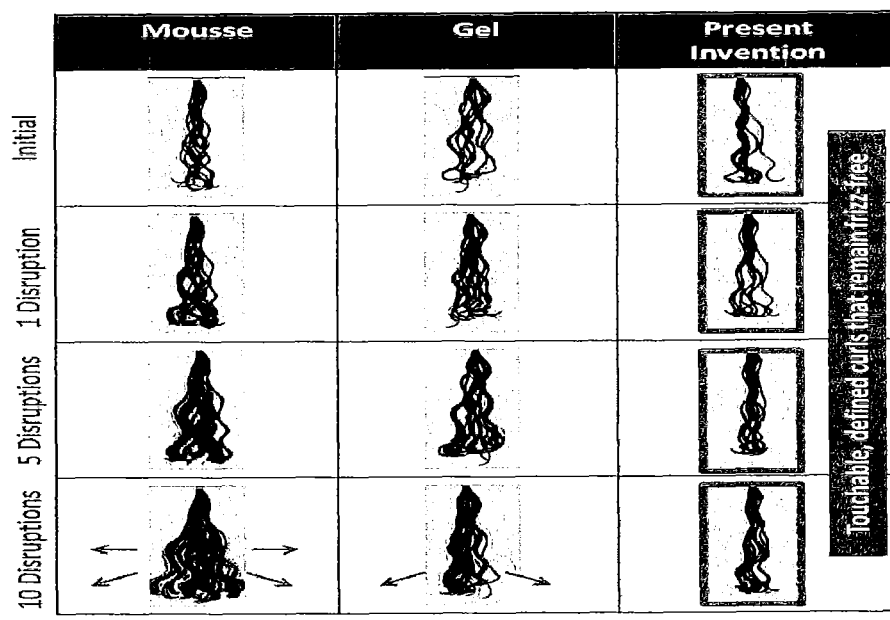

Regarding the photographs in FIG. 1B, the general experimental approach described above was used, with the following specific conditions:
Method: Curl Disruption
  Wavy tresses-15 g
  Amount applied-1.5 g
  Allow to air dry overnight after application
  Gently comb fingers through hair capturing pictures at 1, 5, and 10 disruptions
Conclusions:
  The mousse tress became the most frizzy, expanding and becoming poufy and lost its curl definition after combing fingers through.
  The gel tress became slightly frizzy (mainly at the ends) and looks more like one bundle rather than individual smaller bundles
  The cream composition (present invention) tress retained its curl definition and didn't become frizzy through 10 disruptions.

Figure 1C:
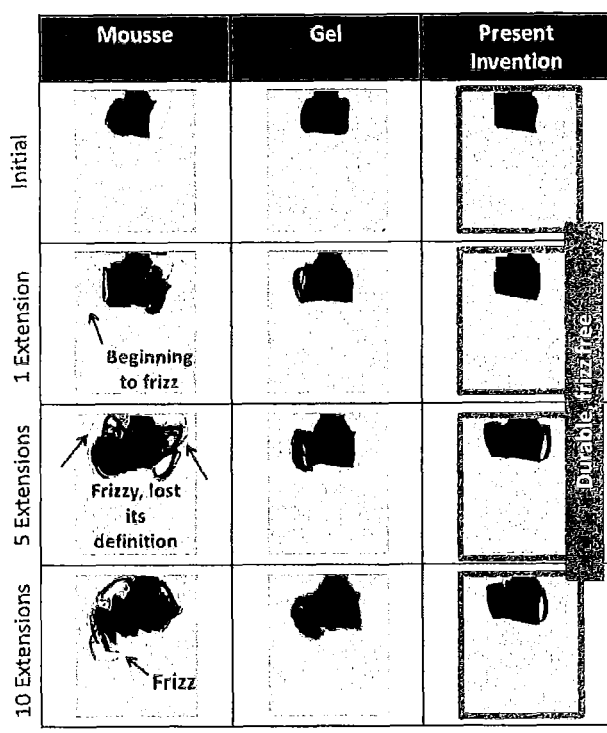

Regarding the photographs in FIG. 1C, the general experimental approach described above was used, with the following specific conditions:
Method: Curl Disruption:
  Average tress-5 g
  Amount applied-0.50 g
  Apply test product and wrap hair around roller and clip in place
  Allow to air dry overnight
  Place finger in curl opening and gently straighten the tress
  Capture pictures after 1, 5, and 10 extensions
Conclusions:
  The mousse tress started becoming frizzy after just one extension and completely lost its definition after 5 extensions.
  The gel tress remained intact and defined up to the 10$^{th}$ extension in which it began to separate slightly.
  The present invention tress had very slight separation after 5 extensions, but remained frizz free.

Figure 1D:
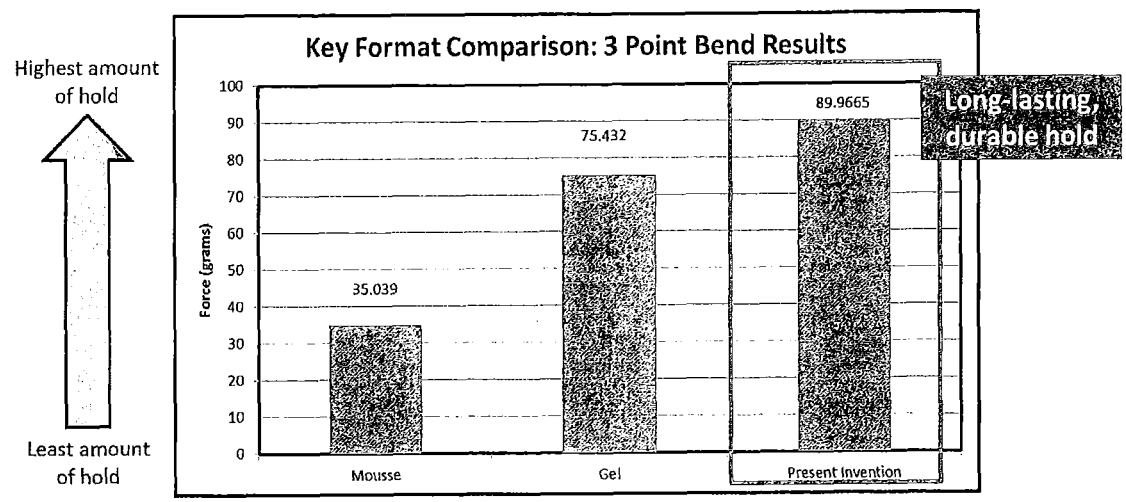

Regarding the graph in FIG. 1D, the general experimental approach described above was used, with the following specific conditions:
Method: 3 Point Bend
  Straight, flat tabbed tress-5 g
  Amount applied: 0.50 g
  Allow tress to air dry overnight after application
  Using Texture Analyzer, evaluate the average maximum force over 10 deformations
Conclusion:
  The compositions of the present invention withstand a significantly higher force than did the conventional mousse and gel products.

What is claimed is:

1. A cosmetic hair styling cream composition consisting of: (A) disodium EDTA present at from 0.00% to 0.10% by weight of the cream composition; (B) hydroxypropyl methylcellulose present at from 1.00% to 5.00% by weight of the cream composition; (C) sodium polystyrene sulfonate present at from 1.00% to 5.00% by weight of the cream composition; (D) ceteareth-25 present at from 0.10% to 1.00% by weight of the cream composition; (E) cetearyl alcohol present at from 1.00% to 5.00% by weight of the cream composition; (F) stearyl alcohol present at from 0.10% to 1.00% by weight of the cream composition; (G) behenyl alcohol present at from 0.00% to 0.10% by weight of the cream composition; (H) cetyl alcohol present at from 0.10% to 1.00% by weight of the cream composition; (I) polyurethane-34 present at from 1.00% to 5.00% by weight of the cream composition; (J) polyacrylamide, $C_{13-14}$ isoparaffin, and laureth-7 present at from 1.00% to 5.00% by weight of the cream composition; (K) cocotrimonium methosulfate present at from 0.10% to 1.00% by weight of the cream composition; (L) laureth-3 present at from 0.10% to 1.00% by weight of the cream composition; (M) water, silicone quaternium-18, trideceth-6, and trideceth-12 present at from 0.10% to and 1.00% by weight of the cream composition; (N) preservative present at from 0.10% to 1.00% by weight of the cream composition; (O) jojoba oil present at from 0.10% to 1.00% by weight of the cream composition; (P) abysinnian oil present at from 0.00% to 0.10% by weight of the cream composition; (Q) fragrance present at from 0.00% to 0.10% by weight of the cream composition; and (R) deionized water to total the cream composition to 100% by weight.

2. The cream composition according to claim 1, having a viscosity of from 15,000 to 40,000 cps.

3. A method of styling hair comprising applying a hair-styling effective amount of the cream composition according to claim 1 to hair.

4. The method according to claim 3 wherein the cream composition is applied to damp hair.

5. The method according to claim 4 wherein 2 g to 8 g of the cream composition is placed into hands and applied to the hair.

6. The method according to claim 5 wherein the hair is allowed to air dry after application of the cream composition.

7. The method according to claim 3 wherein the hair is not subjected to high temperature heating after application of the cream composition.

* * * * *